United States Patent
Powlan

(10) Patent No.: US 8,262,709 B1
(45) Date of Patent: Sep. 11, 2012

(54) DEVICE AND METHOD FOR FEMORAL NECK FRACTURE FIXATION

(76) Inventor: Roy Y. Powlan, Lafayette, CA (US)

( * ) Notice: Subject to any disclaimer, the term of this patent is extended or adjusted under 35 U.S.C. 154(b) by 0 days.

(21) Appl. No.: 13/200,489

(22) Filed: Sep. 24, 2011

(51) Int. Cl.
- *A61B 17/88* (2006.01)
- *A61B 17/80* (2006.01)
- *A61B 17/04* (2006.01)
- *A61B 17/86* (2006.01)
- *A61B 17/84* (2006.01)
- *A61F 2/08* (2006.01)
- *A61F 2/32* (2006.01)

(52) U.S. Cl. ........ 606/281; 606/329; 606/286; 623/22.4

(58) Field of Classification Search ............ 606/104, 606/281, 286, 329; 623/20.35, 20.36, 22.4, 623/22.41

See application file for complete search history.

(56) References Cited

U.S. PATENT DOCUMENTS

| | | | |
|---|---|---|---|
| 3,094,120 A | 6/1963 | Blosser | |
| 3,486,500 A * | 12/1969 | Ball Kenneth et al. | 606/67 |
| 3,781,917 A * | 1/1974 | Mathys | 623/23.27 |
| 3,939,498 A * | 2/1976 | Lee et al. | 623/23.27 |
| 4,153,953 A * | 5/1979 | Grobbelaar | 623/23.27 |
| 4,465,065 A * | 8/1984 | Gotfried | 606/65 |
| 4,605,416 A * | 8/1986 | Grobbelaar | 623/23.27 |
| 4,698,063 A * | 10/1987 | Link et al. | 623/23.22 |
| 5,167,666 A * | 12/1992 | Mattheck et al. | 623/23.27 |
| 5,429,641 A * | 7/1995 | Gotfried | 606/67 |
| 5,458,654 A * | 10/1995 | Tepic | 623/23.27 |
| 6,409,768 B1 * | 6/2002 | Tepic et al. | 623/23.27 |
| 6,503,281 B1 * | 1/2003 | Mallory | 623/22.15 |
| 7,179,259 B1 * | 2/2007 | Gibbs | 606/64 |
| 7,927,333 B2 | 4/2011 | Gradl | |
| 2007/0219636 A1 | 9/2007 | Thakkar | |
| 2010/0036431 A1 | 2/2010 | Haidukewych | |
| 2010/0174285 A1 | 7/2010 | Probe | |

OTHER PUBLICATIONS

Minimally displaced intra-capsular femoral neck fractures in th elderly,Journal of Orthopedic Surgery,2003;11(2);129-136.

\* cited by examiner

*Primary Examiner* — Kevin T Truong
*Assistant Examiner* — David Bates

(57) ABSTRACT

A device and method for the stabilization of the shafts of threaded hip pins in the treatment of intracapsular fractures of the neck of the femur, using an intertrochanteric hip pin stabilizing rod, a cortical side plate with a releasably attached drill and insertion tool jig, said jig comprising a means for accurately inserting said rod and a plurality of parallel threaded hip pins through openings in the jig, the cortical side plate, and the intertrochanteric pin stabilizing rod, across the fracture and into the head of the femur.

11 Claims, 3 Drawing Sheets

DEVICE AND METHOD FOR FEMORAL NECK FRACTURE FIXATION

BACKGROUND

Prior Art

The following is a tabulation of some prior art that presently appears relevant:
U.S. Patents

| U.S. Pat. No. | Kind Code | Issue Date | Patentee |
| --- | --- | --- | --- |
| U.S. Pat. No. 3,094,120 | B1 | Jun. 18, 1963 | Blosser |
| U.S. Pat. No. 7,927,333 | B2 | Apr. 19, 2011 | Gradl |

U.S. Patent Application Publications

| Publication Nr. | Kind Code | Publ. Date | Applicant |
| --- | --- | --- | --- |
| U.S. 2007/0219636 | A1 | Sep. 20, 2007 | Thakkar |
| U.S. 2010/0036431 | A1 | Feb. 11, 2010 | Haidukewych |
| U.S. 2010/0174285 | A1 | Jul. 08, 2010 | Probe |

Non-Patent Literature Documents

Minimally displaced intra-capsular femoral neck fractures in the elderly-comparison of multiple threaded pins and sliding compression screws surgical techniques; Dr. Chi Chuan Wu, Journal of Orthopedic Surgery, 2003; (2); 129-136.

BACKGROUND

Fractures of the femoral neck at the hip joint are one of the most frequent fractures in elderly women, the result of osteoporosis, the thinning of bone tissue and the loss of bone density. The blood supply to the head of the femur is very precarious, and it tends to become more so as one gets older, and as a result, a good percentage of the hip fractures of the elderly will not heal regardless of the method of treatment. Because of this dilemma, many surgeons elect to not try to heal the fracture, but instead, replace the head of the bone with a prosthesis. While this arthroplasty may function sufficiently well for the older, more sedentary patients, it may not be adequate for the needs of younger more active patients, as it may wear and become painful to the point where further surgery such as total hip replacement may become necessary. To avoid this outcome in this large group of patients, internal fixation surgery to promote healing of the fracture is desirable in certain types of hip fractures. Unfortunately, the currently available means to secure femoral neck fracture fixation are not without significant disadvantages. It has been found that while the use of multiple threaded pins for fixation results in less osteonecrosis of the head of the femur, they result in more non-unions than do sliding compression screws which result in more unions but also cause an increase in the death of the head, probably because of the greater intramedullary vascular damage as a result of wider reaming. These facts would suggest that an increase in the effective rigidity of the multiple threaded hip pins would lead to an increase in the number of unions, and a decrease in the number of femoral head deaths in many patients.

Among the devices used, the earliest where rods or lag screws inserted from the lateral cortex of the femur into the head. Problems with these led to the use of bone plates fastened to their base and fixed to the lateral cortex. Further developments included rods or lag screws with tubular collars that permitted the screw to slide out to compensate for shortening of the neck as healing took place. Also used where multiple threaded pins, some using a cortical side plate in conjunction with the pins to help stabilize them, others using a cortical side plate with elongated pin collars. Unfortunately, pins used in this manner still behave as long cantilevered springs, with little or no support in the osteoporotic neck of the femur, resulting in a lack of complete immobilization of the fracture, and a resulting non-union. Further developments led to the use of single or multiple hip screws supported by intramedullary rods inserted into the medullary canal of the femur from its proximal end. These often used an outrigger type of drill jig attached to the proximal end of the intramedullary rod to drill the openings for, and guide the screws alongside of, or in some instances, through orifices in the rods into the head of the femur. Because of the shaft/neck angle, they do little to support the more distal pins. These devices using an intramedullary rod add yet another element of risk to an already fragile elderly patient with the more extensive surgery, blood loss and anesthesia time required. In addition, the large opening made near the base of the neck of the femur to accommodate the rod could further interfere with the already precarious blood supply to the head and neck of the femur.

SUMMARY OF THE INVENTION

An object of this invention is a device and method for the fixation of fractures of the femoral neck that achieves a rigid fixation of the fracture with limited surgical exposure, resulting in less blood loss and trauma to the patient.

A further object is secure the advantages of the use of a plurality of known threaded hip pins that are less likely to impair the blood supply to the head of the femur rather than the use of large threaded bolts or lag screws that require wider reaming and displacement of much of the vital bone, and which can also cause rotation of the head and fracture separation during their insertion, leading to osteonecrosis of the head of the femur.

A further object is to stabilize the threaded hip pins through the use of an intertrochanteric pin stabilizing rod that is supported at both ends by medial and lateral cortical bone as well as by the inter-trochanteric cancellous bone, and which supports and stabilizes the mid-portion of the hip pins, thereby obtaining the advantages of the use of a plurality of hip pins without their disadvantages, and the advantages of the stiffness of large threaded screws or bolts without their circulation and cancellous bone damaging bulk.

Another object is to stabilize the hip pins even further with the use of a cortical bone plate that supports the hip pins at their point of entry into the lateral cortex of the femur.

A further object is to provide a means for the placement of the intertrochanteric pin stabilizing rod comprising a drill and insertion tool jig that when fastened to the cortical bone plate, permits an intertrochanteric osseous channel to be made from the lateral cortex of the greater trochanter, through the medulla, and into the medial femoral cortex in the immediate vicinity of the lesser trochanter.

A further object is to enable a detachable drill and insertion tool jig to also function as a guide for the insertion of threaded hip pins, thereby eliminating the need for prior art thick cortical bone plates, and plates with bulky integral pin collars.

To accomplish these objectives, this invention employs a concept of femoral neck fracture fixation that is not taught by the prior art. In a preferred embodiment, an elongate cortical bone plate with three equally spaced and aligned, angled openings for the passage of threaded hip pins near its proximal end is affixed to the lateral cortex of the femur, positioned so that the longitudinal axis of the middle opening passes through the middle of the femoral neck, following which, a drill and insertion tool jig comprising an elongate leg distally with a means for its releasable attachment to the cortical bone plate, and a tubular drill guide proximally which is angularly directed and positioned adjacent to the lateral cortex of the greater trochanter with its longitudinal axis directed from the greater trochanter towards the medial cortex of the femur in the immediate vicinity of the lesser trochanter, is releasably affixed to the cortical bone plate.

A channel is then drilled through the lateral cortex of the greater trochanter towards and into the medial femoral cortex in the area of the lesser trochanter. A drill bit commonly known as a "step drill" enables a smaller diameter opening to be made in the medial cortex.

An insertion tool comprising an elongate cylindrical rod with an integral cap proximally and a means for the releasable attachment to an intertrochanteric pin stabilizing rod distally, and with a predetermined length, is releasably fastened to the proximal end of an intertrochanteric pin stabilizing rod, which comprises an elongate cylindrical rod of predetermined length with its proximal end having a means for the releasable attachment to the insertion tool, and its distal end having a means for its engagement with the medial femoral cortex, and with a plurality of equally spaced transverse openings through the middle portion of the rod, each dimensioned for the sliding fit of threaded hip pins.

The intertrochanteric pin stabilizing rod with the attached insertion tool is then inserted into, and translated through the tubular drill guide into the prepared intertrochanteric osseous channel, the extent of its translation being limited by the proximal end cap of the insertion tool, thus enabling the openings in the intertrochanteric pin stabilizing rod, those in the cortical bone plate, and those in the side plate of the drill and insertion tool jig to become coaxially aligned, permitting a plurality of threaded hip pins to be inserted through their openings and into the head of the femur. After the threaded hip pins have been inserted, the hip pin intertrochanteric stabilizing rod can no longer rotate around its long axis, thus permitting the detachment and removal of both the insertion tool and the drill and insertion tool jig.

The result is a rigid assembly wherein the hip pin intertrochanteric stabilizing rod is locked in cancellous and cortical bone at both ends, which in turn supports and unlike the prior art, stabilizes the mid-portion of all of the threaded hip pins, thus reducing the long cantilever springiness of the pins, which promotes healing of the fracture by reducing micromotion at the fracture site. Since all of the pins are held together as a unit, the pins tend to support each other adding to their effective stiffness. In addition, being parallel, the pins are able to slide outwardly during healing of the fracture.

DETAILED DESCRIPTION OF THE DRAWINGS

Figure 1:
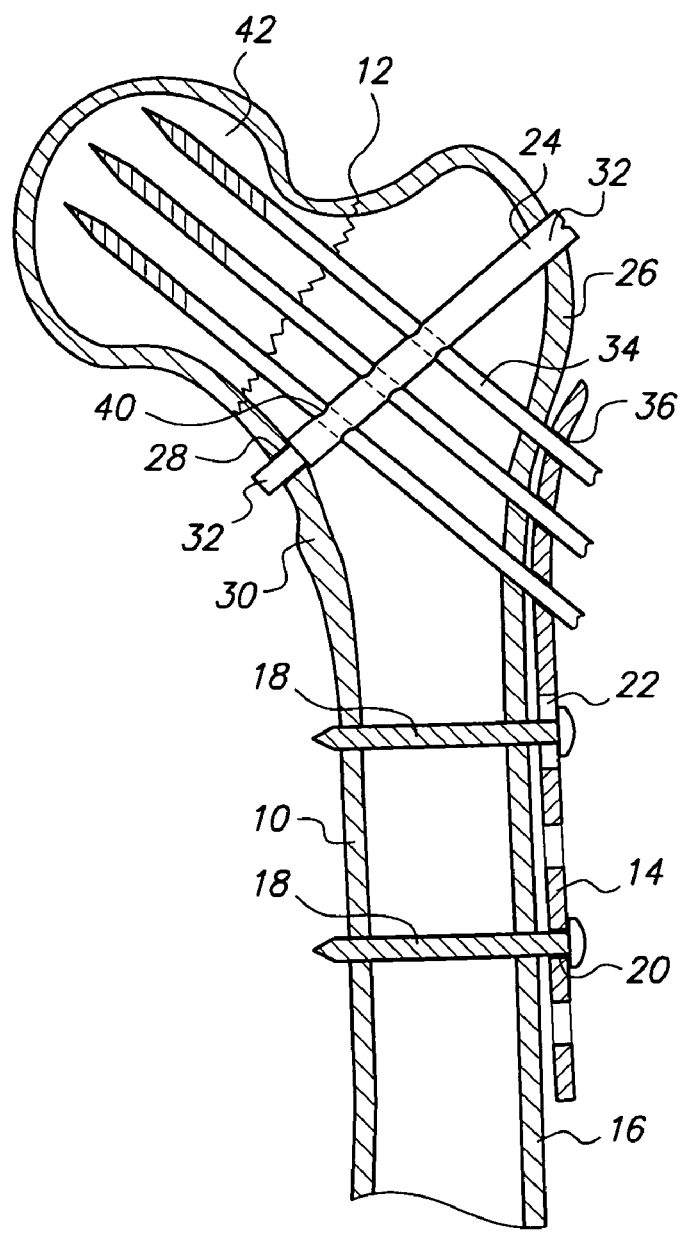
FIG. 1 is a frontal sectional view of a proximal femur with a sub-capital fracture, with the hip pin intertrochanteric stabilizing rod, the cortical bone plate and three threaded hip pins having been inserted.

For convenience, the same or equivalent elements in the various embodiments of the invention illustrated in the drawings have been identified with the same reference numerals. Further, in the description that follows, any reference to exact dimensions or particular construction materials shown herein are examples of suitable configurations only, and not intended to be limiting in any way. Depending on the needs of any particular application, those skilled in the art will readily recognize, in light of the following teachings, a great many suitable alternative implementation details. In the following description, any reference to orientation or direction is intended solely for the convenience of the description and is not intended in any way to limit the scope of the invention.

FIG. 1 shows one embodiment of the invention. The proximal end of an exemplary femur 10 shows a fracture 12 through the base of the neck of the bone. A cortical bone plate 14 has been affixed to the lateral cortex 16 of the femur with two screws 18 through openings 20 and 22. Opening 22 is elongated to allow longitudinal fine adjustment of the plate 14 before the screw is tightened down. The intertrochanteric pin stabilizing rod 24 has been inserted through the lateral cortex of the greater trochanter 26, and its tip 32 has been directed into the opening 28 in the medial femoral cortex 58 in the area of the lesser trochanter 30. Both ends of the intertrochanteric pin stabilizing rod 24 are supported by cortical bone, which in turn, supports the threaded hip pins 34 and minimizes their tendency to bend and twist in the osteoporotic cancellous bone. The notch 70 is an indicator of the rotational orientation of the rod 24 to assist in the insertion of the hip pins 34

FIG. 1 also shows three known threaded hip pins 34 having been inserted through the openings 36 in the cortical bone plate 14. It should be noted that the location and angle of the longitudinal axis of the openings 40 in the intertrochanteric pin stabilizing rod 24 have been precisely determined in relation to the pin openings in the cortical bone plate 36. It should also be noted that the hip pins 34 are parallel to each other. This is important because it allows the pins to slide outwardly as healing of the fracture takes place with some resultant shortening of the femoral neck.

Figure 2:
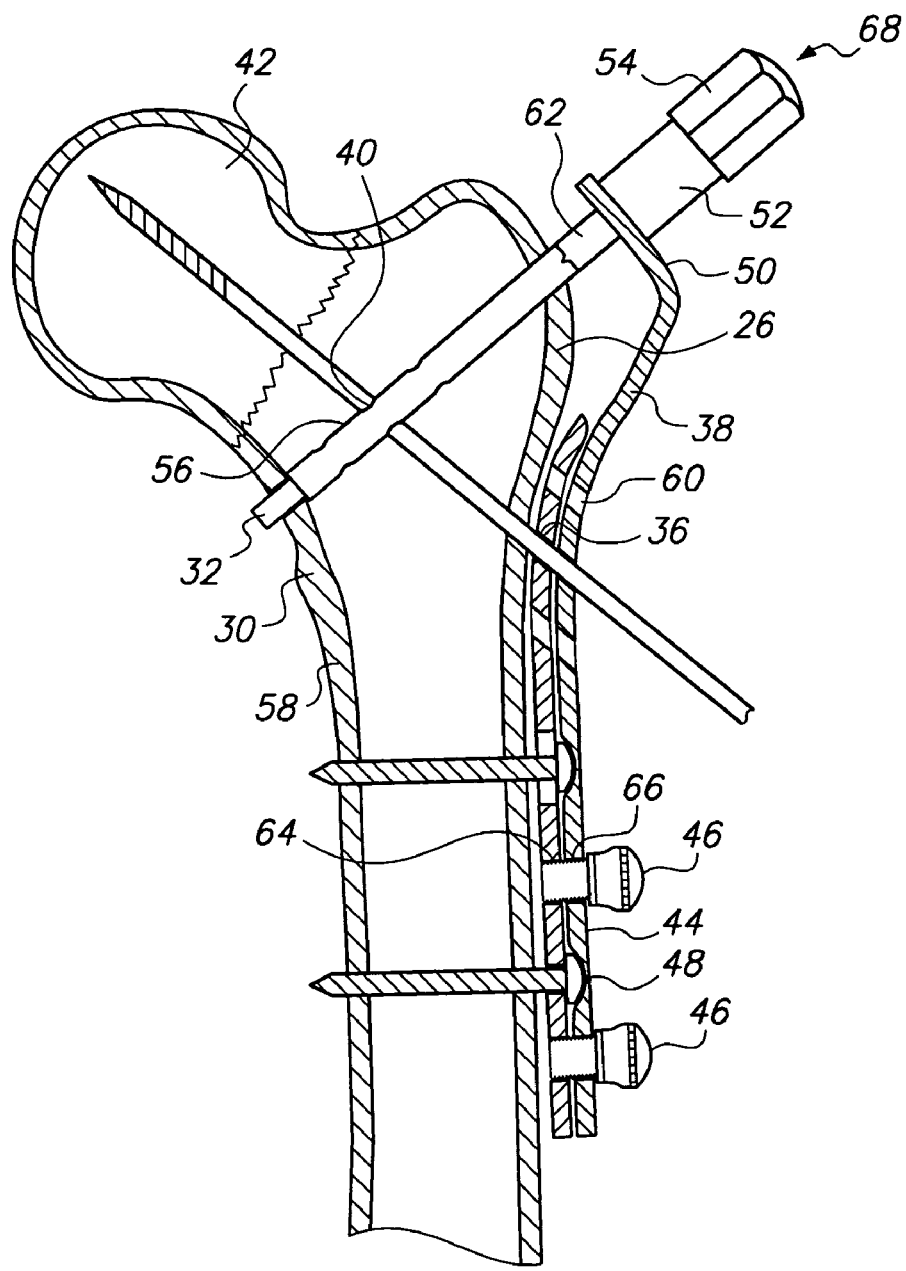
FIG. 2 is a frontal sectional view of a proximal femur with a sub-capital fracture. A cortical bone plate is held in place with two screws. The intertrochanteric pin stabilizing rod, the insertion tool and the drill and insertion tool jig are shown in place. One threaded hip pin has been inserted.

FIG. 2 shows the method by which the drill and insertion tool jig 38 is employed to accurately insert the intertrochanteric pin stabilizing rod 24. Shown is a proximal femur 10, femoral head 42 and fracture 12. As shown in FIG. 1, a cortical bone plate 14 has been affixed to the lateral femoral cortex 16. It should be noted that the cortical bone plate has several functions as compared to the prior art. It comprises the basis for the attachment of the drill and insertion tool jig, which determines the exact placement of the intertrochanteric pin stabilizing rod. Also, the longitudinal axes of the openings 36 are coaxial with the longitudinal axes of the openings 40 of the intertrochanteric pin stabilizing rod so that the hip pins can easily be inserted through both of them. Also, after the hip pins have been inserted into the head of the femur, the gripping of the hip pins by the cortical bone plate prevents rocking motion of the pins in the intertrochanteric pin stabilizing rod, and contributes to the overall effective stiffness of the pins.

The elongated side plate 44 of the drill and insertion tool jig 38 has been releasably attached to the cortical bone plate 44 with two known threaded fasteners 46. The surface of the side plate 44 facing the cortical bone plate 14 has screw-head indentations 48 to avoid interference with them. The proximal end 50 of the drill and insertion tool jig 38 comprises a tubular drill guide 52, that is located adjacent to the greater trochanter 26, with its longitudinal axis directed towards the area of the lesser trochanter 30. The intertrochanteric pin stabilizing rod 24 is shown attached to the insertion tool 54, and has been inserted into the drilled intertrochanteric osseous channel 56 to engage with the medial femoral cortex 58. One threaded hip pin 34 has been inserted through a guide opening 60 in the elongate side plate 44, through the opening 36 in the cortical bone plate 14, through the chamfered pin opening 40 in the intertrochanteric pin stabilizing rod 24 and into the head of the femur 42. Following the insertion of a plurality of hip pins, three in a preferred embodiment, the insertion tool 54 is detached and removed. The two threaded fasteners 46 are detached and the drill and insertion tool jig 38 is removed, following which the excess length of the threaded hip pins 34 are trimmed off, completing the operation.

Figure 3:
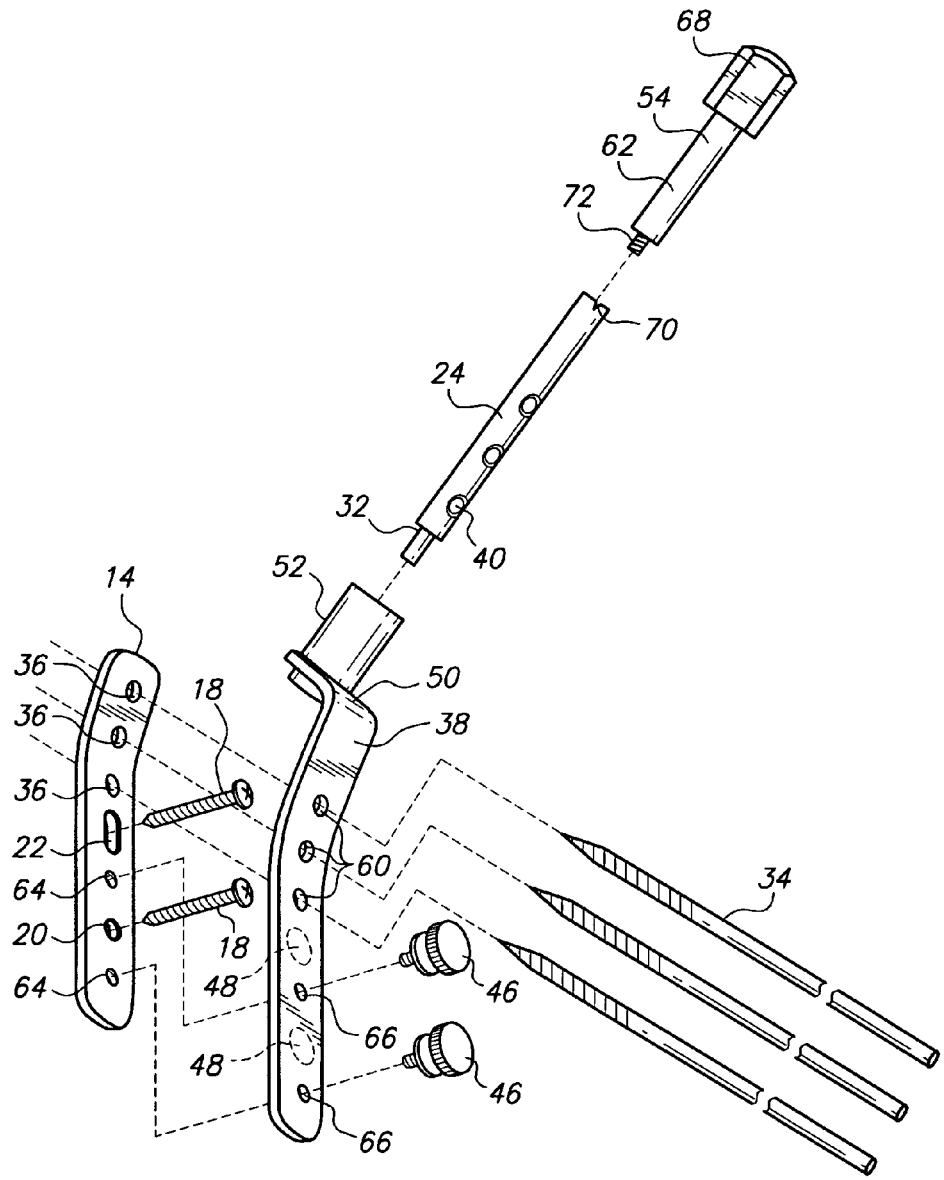
FIG. 3 is an exploded view of the femoral neck fracture fixation device, including a cortical bone plate with two screws, a drill and insertion tool jig with two threaded fasteners for attachment to the cortical bone plate, an intertrochanteric pin stabilizing rod, a rod insertion tool, and fragments of three threaded hip pins.

FIG. 3 is an exploded view of the drill and insertion tool jig 38, showing a tubular drill guide 52 at its proximal end, together with an exemplary intertrochanteric pin stabilizing rod 24 and its insertion tool 54. Shown is the means for releasable attachment 72 of the insertion tool to the intertrochanteric pin stabilizing rod. The predetermined diameter of the pin stabilizing rod 24 and the insertion tool 54 are a sliding fit into the tubular drill guide 52. The predetermined length of the intertrochanteric pin stabilizing rod 24 and the predetermined configuration of the chamfered pin openings 40 through it, together with the predetermined length of the insertion tool shaft 62 determine the exact angle and location of the intertrochanteric pin stabilizing rod 24 within the intertrochanteric region of the femur, enabling threaded hip pins 34 inserted through the angled guide openings 60 of the drill and insertion tool jig, through the angled openings 36 in the cortical bone plate 14, through the chamfered pin openings 40 in the intertrochanteric pin stabilizing rod 24, and across the fracture 12, to enter into the femoral head 42. The pin openings 40 are chamfered to facilitate insertion of the threaded hip pins.

Also shown in FIG. 3 is the cortical bone plate 14 and means for fastening it to the lateral femoral cortex. The proximal screw opening 20 is elongated to enable longitudinal fine adjustment of the plate. The proximal end of the cortical bone plate 14 comprises a plurality of angled openings 36, three in this embodiment, dimensioned for threaded hip pins 34. It also comprises two threaded openings 64 for the releasable attachment of the elongate side plate 44 of the drill and insertion tool jig 38.

Shown further in FIG. 3 are details of the elongate side plate 44 of the drill and insertion tool jig 38. It comprises two openings 66 for its releasable attachment by two threaded fasteners 46. It also comprises three guide openings 60 for the passage of the threaded hip pins 34. As noted above, unlike some prior art, the drill and insertion tool jig with its guide openings is removed after the threaded hip pins have been inserted, thereby avoiding the disadvantage of having a bulky plate and pin collars which in a thin patient can result in subcutaneous irritation.

Also shown in FIG. 3 are two indentations 48 in the side of the elongate side plate 44 facing the cortical bone plate 14 to accommodate the heads of screws 18. Fragments of three threaded hip pins 34 are shown prior to their entry through the guide openings 60 and the openings 36 in the cortical bone plate.

FIG. 3 also shows a notch 70 in the circumference of the first end of the intertrochanteric pin stabilizing rod 24 which is a visual indicator of the rotational orientation of the rod, to help in the insertion of the threaded hip pins 34, into the chamfered openings 40 of the intertrochanteric pin stabilizing rod.

PART NAME

| | |
|---|---|
| 10 | Proximal Femur |
| 12 | Fracture |
| 14 | Cortical bone plate |
| 16 | Lateral femoral cortex |
| 18 | Screws |
| 20 | Opening for a screw |
| 22 | Screw opening in cortical bone plate |
| 24 | Intertrochanteric pin stabilizing rod |
| 26 | Greater trochanter |
| 28 | Opening in lesser trochanter |
| 30 | Lesser trochanter |
| 32 | Tip of pin stabilizing rod |
| 34 | Threaded hip pins |
| 36 | Openings for hip pins |
| 38 | Drill and insertion tool jig |
| 40 | Chamfered openings in pin stabilizing rod |
| 42 | Femoral head |
| 44 | Elongate side plate |
| 46 | Threaded fasteners |
| 48 | Indentations for screw heads |
| 50 | Proximal end of drill and insertion tool jig |
| 52 | Tubular drill guide |
| 54 | Insertion tool |
| 56 | Drilled intertrochanteric osseous channel |
| 58 | Medial femoral cortex |
| 60 | Pin guide opening in side plate |
| 62 | Insertion tool shaft |
| 64 | Threaded opening for thumb screws |
| 66 | Side plate openings for thumb screws |
| 68 | Insertion tool cap |
| 70 | Indicator notch |
| 72 | Means for attaching insertion tool to pin stabilizing rod |

What I claim is:

1. An orthopedic apparatus for the fixation of femoral neck fractures, comprising:
   an elongate generally cylindrical intertrochanteric pin stabilizing rod having a first end and a second end defining a longitudinal axis therebetween, wherein the intertrochanteric pin stabilizing rod comprises a plurality of transverse equally spaced openings between the first and second ends of said intertrochanteric pin stabilizing rod;
   means for inserting said intertrochanteric pin stabilizing rod into the intertrochanteric cortical and cancellous bone of the proximal femur, comprising:
      means for the releasable attachment of the first end of said intertrochanteric pin stabilizing rod to an insertion tool;
   means for the engagement of the second end of said intertrochanteric pin stabilizing rod with the bone of the medial femoral cortex;
   a plurality of threaded hip pins;
   an elongate cortical bone plate with a first end and a second end, the elongate cortical bone plate comprising a means for its attachment to the lateral femoral cortex and comprising a plurality of angularly directed openings, each of the plurality of angularly directed openings dimensioned for a sliding fit with the threaded hip pins therethrough, and the elongate cortical bone plate comprising a means for the releasable attachment of a drill and insertion tool jig;

a drill and insertion tool jig comprising an elongate plate with a first end and a second end, the first end comprising a tubular drill guide and the second end comprising a means for the attachment of said jig to the cortical bone plate, and a plurality of angularly directed openings coaxial with the plurality of angularly directed openings in the cortical bone plate when the drill and insertion tool jig is assembled to the cortical bone plate, each of the plurality of angularly directed openings dimensioned for the sliding fit with the threaded hip pins;

wherein said tubular drill guide is configured to be positioned adjacent to the lateral cortex of the greater trochanter of the femur; and an insertion tool comprising an elongate cylindrical rod with a first end and a second end, the first end of the insertion tool comprising a means for limiting the extent of the translation of the rod through said tubular drill guide, said means comprising an integral cap, and the second end comprising a means for releasable attachment of the second end of the insertion tool to the first end of said intertrochanteric pin stabilizing rod, said means comprising a threaded protuberance.

2. The orthopedic apparatus of claim 1, wherein the longitudinal axis of the bore of said tubular drill guide is configured to be directed from the lateral cortex of the greater trochanter towards the medial femoral cortex in the vicinity of the lesser trochanter when the apparatus is in its working configuration.

3. The orthopedic apparatus of claim 1, wherein the second end of the intertrochanteric pin stabilizing rod comprises a circumferentially stepped means configured for rigid engagement with the medial femoral cortex.

4. The orthopedic apparatus of claim 1, wherein the intertrochanteric pin stabilizing rod and the insertion tool are dimensioned to be configured for a sliding fit within the tubular drill guide.

5. The orthopedic apparatus of claim 1, wherein said transverse openings in said intertrochanteric pin stabilizing rod comprise chamfered inlets.

6. The orthopedic apparatus of claim 1, wherein the first end of said intertrochanteric pin stabilizing rod comprises a notch, said notch comprising an indicator of the rotational orientation of said intertrochanteric in stabilizing rod.

7. The orthopedic apparatus of claim 1, wherein said plurality of transverse equally spaced openings of the intertrochanteric pin stabilizing rod comprise three transverse openings.

8. The orthopedic apparatus of claim 1, wherein the angularly directed openings of the cortical bone plate and the angularly directed openings of the drill and insertion tool jig each comprise three said angularly directed openings.

9. A method of fixation of a femoral neck fracture in a patient, comprising the steps of:
a. affixing an elongate cortical bone plate to the lateral cortex of the proximal femur and providing a drill and insertion tool jig, said cortical bone plate comprising a plurality of angularly directed openings for the translation of a plurality of threaded hip pins therethrough, and a means for the releasable attachment of the drill and insertion tool jig, said jig comprising a first end and a second end, the first end comprising a tubular drill guide, and the second end comprising a means for its releasable attachment to the cortical bone plate, and the drill and insertion tool jig comprising a plurality of angularly directed openings between the first and second ends, said angularly directed openings coaxial with the angularly directed openings in the cortical bone plate, said tubular drill guide configured to be positioned adjacent to the lateral cortex of the greater trochanter of the patient and with the long axis of a bore of the tubular drill guide directed towards the medial femoral cortex in the vicinity of the lesser trochanter;
b. attaching the drill and insertion tool jig to the cortical bone plate;
c. drilling an osseous channel through the lateral cortex of the greater trochanter towards and into the medial femoral cortex in the vicinity of the lesser trochanter;
d. attaching the distal end of an insertion tool to the proximal end of an intertrochanteric pin stabilizing rod, said insertion tool comprising an elongate rod of predetermined length and diameter with a first end and a second end, said first end comprising a means for limiting the extent of translation of the rod through said tubular drill guide, said means comprising an integral cap, and the second end comprising a means for the releasable attachment of the rod to the proximal end of said intertrochanteric pin stabilizing rod, said intertrochanteric in stabilizing rod having a first end and a second end, the first end comprising a means for its releasable attachment to the second end of the insertion tool, and the second end comprising a means for its rigid engagement with the medial femoral cortex, said means comprising an elongate protuberance, and the intertrochanteric in stabilizing rod comprising a plurality of transverse openings between the first and second ends, said openings dimensioned for a sliding fit with threaded hip pins, and with the longitudinal axes of said transverse openings coaxial with the angularly directed openings in the cortical bone plate and with the angularly directed openings in the drill and insertion tool jig;
e. inserting the said intertrochanteric pin stabilizing rod with the attached said insertion tool through said tubular drill guide into the drilled osseous channel;
f. inserting a plurality of hip pins through said angularly directed openings in the drill and insertion tool jig, and through the said angularly directed openings in said cortical bone plate, and through the said transverse openings in the said intertrochanteric pin stabilizing rod, across the fracture and into the head of the femur;
g. detaching and removing the insertion tool from the intertrochanteric pin stabilizing rod; and
h. detaching and removing the drill and insertion tool jig, thereby creating a rigid assembly in which the intertrochanteric pin stabilizing rod is locked into femoral cortical bone at both ends, which in turn supports and stabilizes the threaded hip pins, thereby immobilizing the fracture of the neck of the femur.

10. The method of claim 9, wherein the plurality of transverse openings of the intertrochanteric pin stabilizing rod comprises three transverse openings, said openings comprising chamfered inlets.

11. The method of claim 9 wherein the plurality of angularly directed openings of the cortical bone plate and the plurality of angularly directed openings of the drill and insertion tool jig each comprise three angularly directed openings.

* * * * *